(12) United States Patent
Butterfield et al.

(10) Patent No.: US 7,879,056 B2
(45) Date of Patent: Feb. 1, 2011

(54) PLEURABRADE DEVICE

(76) Inventors: Keith Butterfield, 46 Cushman St., Portland, ME (US) 04102; Kevin Butterfield, P.O. Box 98, Raymond, ME (US) 04071

( * ) Notice: Subject to any disclaimer, the term of this patent is extended or adjusted under 35 U.S.C. 154(b) by 292 days.

(21) Appl. No.: 11/974,096

(22) Filed: Oct. 11, 2007

(65) Prior Publication Data
US 2009/0099583 A1 Apr. 16, 2009

(51) Int. Cl.
*A61B 17/32* (2006.01)
(52) U.S. Cl. ...................................... 606/170
(58) Field of Classification Search ............... 606/170, 606/113, 159, 161, 167, 110, 127, 200, 171; 600/7; 604/109, 108, 107, 106, 105, 104, 604/22
See application file for complete search history.

(56) References Cited

U.S. PATENT DOCUMENTS

| 5,030,201 | A | | 7/1991 | Palestrant | |
|---|---|---|---|---|---|
| 5,471,982 | A | * | 12/1995 | Edwards et al. | 600/374 |
| 5,755,732 | A | * | 5/1998 | Green et al. | 606/170 |
| 5,868,708 | A | | 2/1999 | Hart et al. | |
| RE36,764 | E | | 7/2000 | Zacca et al. | |
| 6,096,054 | A | * | 8/2000 | Wyzgala et al. | 606/170 |
| 6,626,861 | B1 | | 9/2003 | Hart et al. | |
| 7,357,770 | B1 | * | 4/2008 | Cutrer et al. | 600/3 |
| 2002/0077520 | A1 | * | 6/2002 | Segal et al. | 600/1 |
| 2004/0243023 | A1 | * | 12/2004 | Grigoryants et al. | 600/564 |
| 2006/0224223 | A1 | * | 10/2006 | Podhajsky et al. | 607/117 |
| 2007/0112300 | A1 | | 5/2007 | Roman et al. | |
| 2007/0270627 | A1 | * | 11/2007 | Cutrer et al. | 600/7 |
| 2008/0091055 | A1 | * | 4/2008 | Nguyen et al. | 600/7 |
| 2008/0108859 | A1 | * | 5/2008 | Cutrer et al. | 600/7 |

* cited by examiner

*Primary Examiner*—Anhtuan T Nguyen
*Assistant Examiner*—Katherine M Shi
(74) *Attorney, Agent, or Firm*—J. Wiley Horton

(57) ABSTRACT

An abrading device for use in irritating and blotting a surgical area, preferably the area between the chest wall and lung of a patient, to allow the user to more easily insert and remove the surgical device reducing contact with surrounding tissue and wound edges. The device is primarily comprised of a cannula, a plurality of radial springs, an abrasive tip, an actuator and an adjuster. The actuator is configured to selectively move the abrasive tip and plurality of radial springs into and out of the cannula. The adjuster allows the user to selectively expand or collapse the abrasive tip.

17 Claims, 16 Drawing Sheets

PLEURABRADE DEVICE

CROSS-REFERENCES TO RELATED APPLICATIONS

Not Applicable

STATEMENT REGARDING FEDERALLY SPONSORED RESEARCH OR DEVELOPMENT

Not Applicable

MICROFICHE APPENDIX

Not Applicable

BACKGROUND OF THE INVENTION

1. Field of the Invention

This invention relates to the field of surgical devices. More specifically, this invention comprises an abrading device that is used for creating abrasions on a membrane, such as the pleural membrane.

2. Description of the Related Art

Pleurodesis is a medical procedure in which the pleural space, the space between the chest wall and the lung of a patient, is obliterated. This is commonly done in order to prevent the recurrence of pneumothorax or pleural effusion. Pleurodesis is accomplished by irritating the parietal pleura, thereby creating abrasions on the chest wall, which causes adhesion between the wall and the lung of a patient. Sealing off of the pleural space prevents unwanted fluid or air from entering and occupying the area after the surgery.

Pleurodesis is typically performed during a thoracotomy or a thoracoscopy. Both surgical techniques are used to enter the chest to perform any number of different medical procedures. The difference between the two techniques is related to the size of the incision that is made in the patient. The incision for a thoracotomy is made on the side of the patient's chest and is typically four to six inches long. In a thoracoscopic operation several small incisions, generally ¼ to 1 inch in diameter, are made in different places around the chest.

FIG. 2 shows a prior art thoracoport 32 with a thorascoscope 30 inserted through the thoracoport 32. Thoracoports 32, small tubes or pipe structures, are typically placed into the small incisions through the chest wall to allow for easy insertion of other small instruments, thereby reducing the risk of damage to surrounding tissues during insertion and withdrawal. A thoracoscope 30, or small fiber optical camera, is inserted through at least one of the thoracoports 32 to view the inside of the chest. This minimally invasive operation allows surgeons to have maximum mobility inside the chest without putting pressure on the ribs. It also allows a surgeon to enter and exit the chest with little trauma to the nerves that travel along the bottom edge of each rib. The benefits to patients include reduced post-operative pain, a faster recovery and less scarring.

Upon nearing the end of a thoracotomy or a thoracoscopy, a surgeon would typically perform surgical pleurodesis by irritating the pleural membrane with a rough pad. FIG. 1 illustrates the existing equipment used for this process. Surgeons attach prior art gauze 36 to a prior art Kelly clamp 34 and physically rub the rough pad along the pleural membrane. Kelly clamp 34 is a medical tool that resembles a pair of scissors; however, the blade is replaced by a locking clamp. A surgeon using a Kelly clamp 34 during a thoracotomy would typically have to disturb the incision site and surrounding tissue in order to push the abrasive gauze 36 into the patient's body between the chest wall and lung. This causes an increase in trauma to the surrounding tissue and likely extension of the initial incision site. Additionally, it is difficult to view the tissue that is being irritated, as the insertion of the Kelly clamp 34 blocks the surgeon's view.

Performing surgical pleurodesis at the end of a thoracoscopy is more difficult than in the thoracotomy. Because the incisions are small, a surgeon must stretch the incision site to fit the Kelly clamp 34 down into the pleural membrane. Again, the result is increased trauma, likely incision extension and difficulty in viewing the irritation process. Since the incision site is so small the reader will note that the insertion of the Kelly clamp 34 and rough gauze 36 is difficult and likely causes more trauma to the body than would be caused when working with a larger incision site.

Abrading devices have not previously been small enough to fit through a thoracoport or other small opening. Additionally, the abrading surface, usually a rough pad, has not previously been retractable into a smooth tube. A retractable abrading surface is particularly advantageous because a smooth and thin instrument can enter the patient's body through a thoracoport 32 or other small incision with little to no contact with "wound edges" and can be completely removed from the patient's chest without rubbing against the surrounding tissue. Furthermore, if the device is able to fit through a thoracoport 32, a thoracoscope 30 can be utilized to view the complete abrading process giving the surgeon extensive visibility to properly irritate the chest wall for complete adhesion.

BRIEF SUMMARY OF THE INVENTION

The present invention comprises an abrading device for irritating and blotting a membrane, particularly the pleural membrane. The device is small enough to be inserted and withdrawn through a prior art thoracoport. It includes a proximal end configured to be gripped by a surgeon and a distal end configured to be inserted through a thoracoport into the patient. The distal end includes a collapsible abrasive "spider" housed within a cannula. The spider can be collapsed and withdrawn into the cannula. In this state, the surgeon can insert the distal end through a thoracoport into the pleural space. The surgeon then manipulates adjustment features located on the invention's proximal end to deploy and expand the spider.

Once the spider is deployed and expanded, the surgeon grips the proximal end and manipulates the device so that the spider abrades the walls of the pleural space. The invention's cannula is small enough so that a thorascoscope can remain in the thoracoport with the cannula and be used to observe the abrading process. Once the abrading process is complete, the surgeon can collapse the spider and withdraw it back into the distal end of the cannula. The device can then be withdrawn back through the thoracoport.

Figure 1:
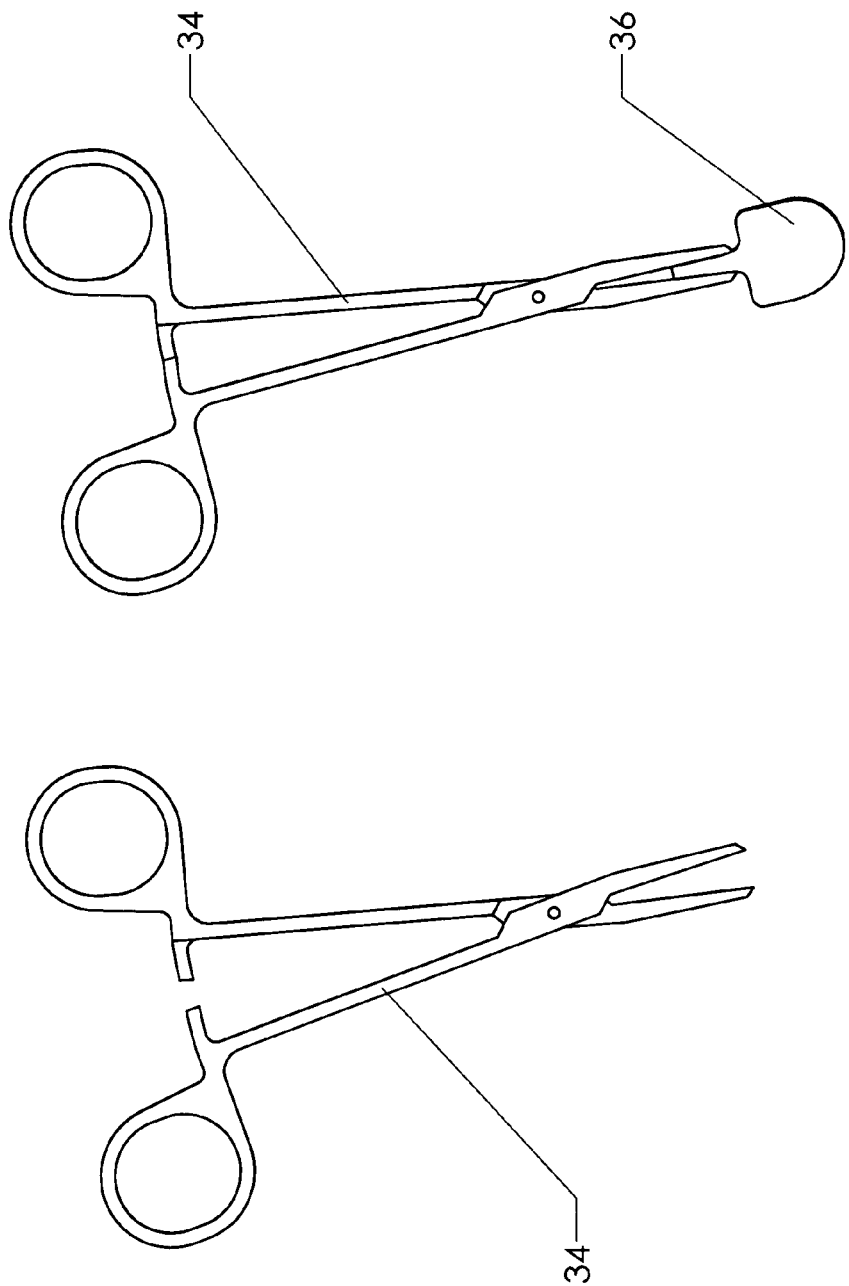
FIG. 1 is a perspective view, showing a prior art Kelly clamp.
Figure 2:
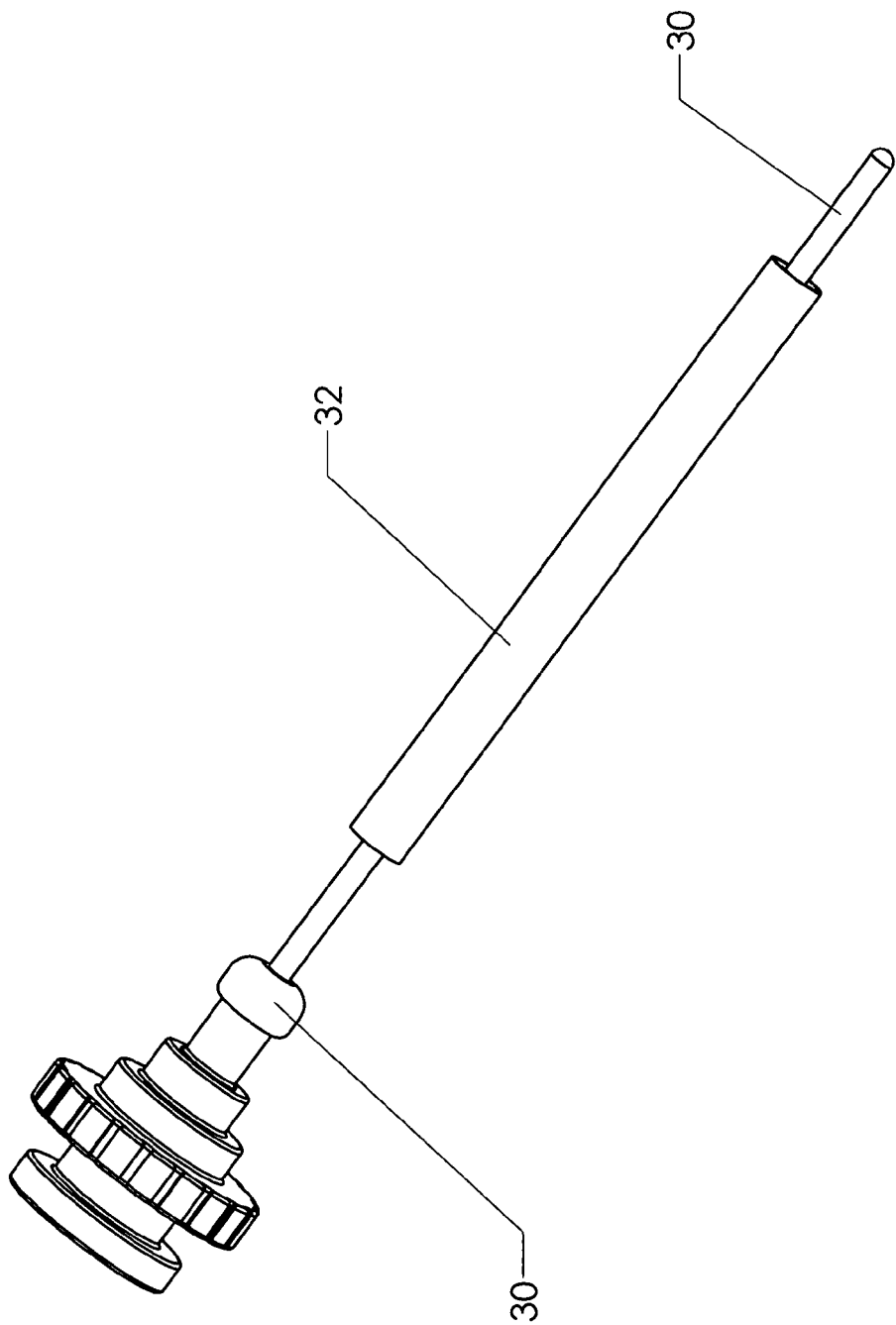
FIG. 2 is a perspective view, showing a prior art thoracoport with a prior art thorascoscope inserted therein.

| REFERENCE NUMERALS IN THE DRAWINGS | | | |
|---|---|---|---|
| 10 | expansion knob | 12 | handle |
| 14 | cannula | 16 | locking collar |
| 18 | abrasive tip | 20 | adjuster |
| 22 | spider | 24 | mechanical assist rod |
| 26 | actuator | 28 | thread engaging key |
| 30 | thorascoscope | 32 | thoracoport |
| 34 | Kelly clamp | 36 | gauze |
| 38 | lever | 40 | lever slot |
| 42 | inner tube | 44 | washer |
| 46 | fastener | 48 | handle assembly |
| 50 | adjuster slot | 52 | thrust flange |
| 54 | helical thread | 56 | lever receiver |
| 58 | radial spring | 60 | hub |
| 64 | hollow receiver | 66 | end wall |

DETAILED DESCRIPTION OF THE INVENTION

Figure 3:
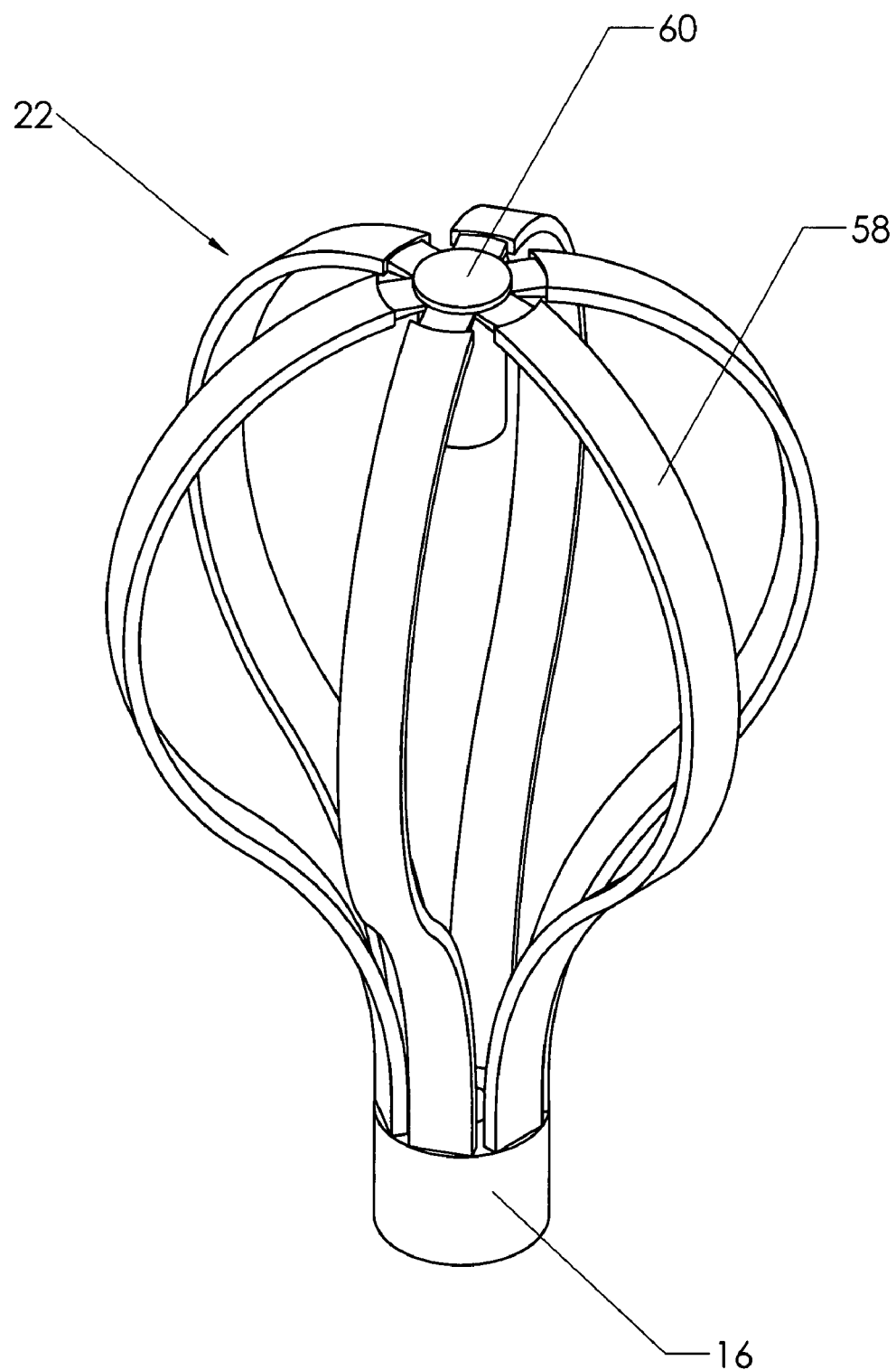
FIG. 3 is a perspective view, showing the abrasive "spider" of the present invention in a fully expanded position.

The present invention is a device for inserting and deploying an expanding abrasive element. FIG. 3 shows the core of this abrasive element, labeled as spider 22. Spider 22 is formed by attaching an array of radial springs 58 to a hub 60 on one end and a locking collar 16 on the opposite end. The springs are made of a thin and resilient material which can undergo substantial deformation without experiencing plastic deformation (an example of a suitable material would be a thin spring steel). By varying the distance between the hub and the locking collar, the radial springs can be selectively bowed outward or collapsed inward. In use, the array of radial springs will be covered by an abrasive (and absorptive) tip which will actually make contact with the surface to be abraded.

Figure 4:
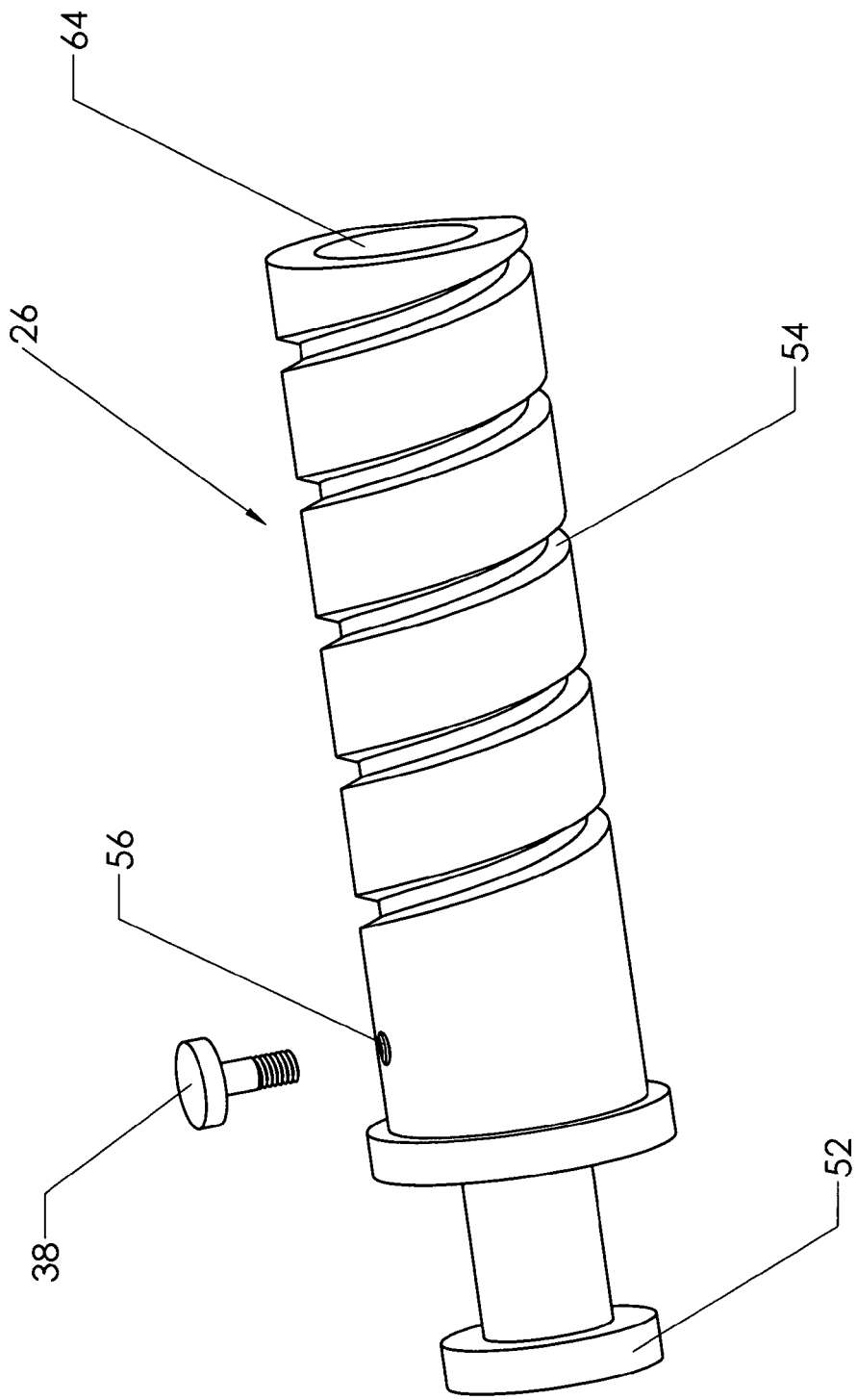
FIG. 4 is a perspective view, showing the actuator.

The components of the invention will now be described in detail, after which the assembly of the components and their subsequent use will be described. FIG. 4 shows actuator 26, which is a generally cylindrical component having a hollow center 64 passing through it from one end to the other. Helical thread 54 is provided over at least a portion of its outer surface. Thrust flange 52 is located on its distal end. A preferably separate lever 38 is configured to lock into lever receiver 56 in the side of actuator 26.

Figure 5:
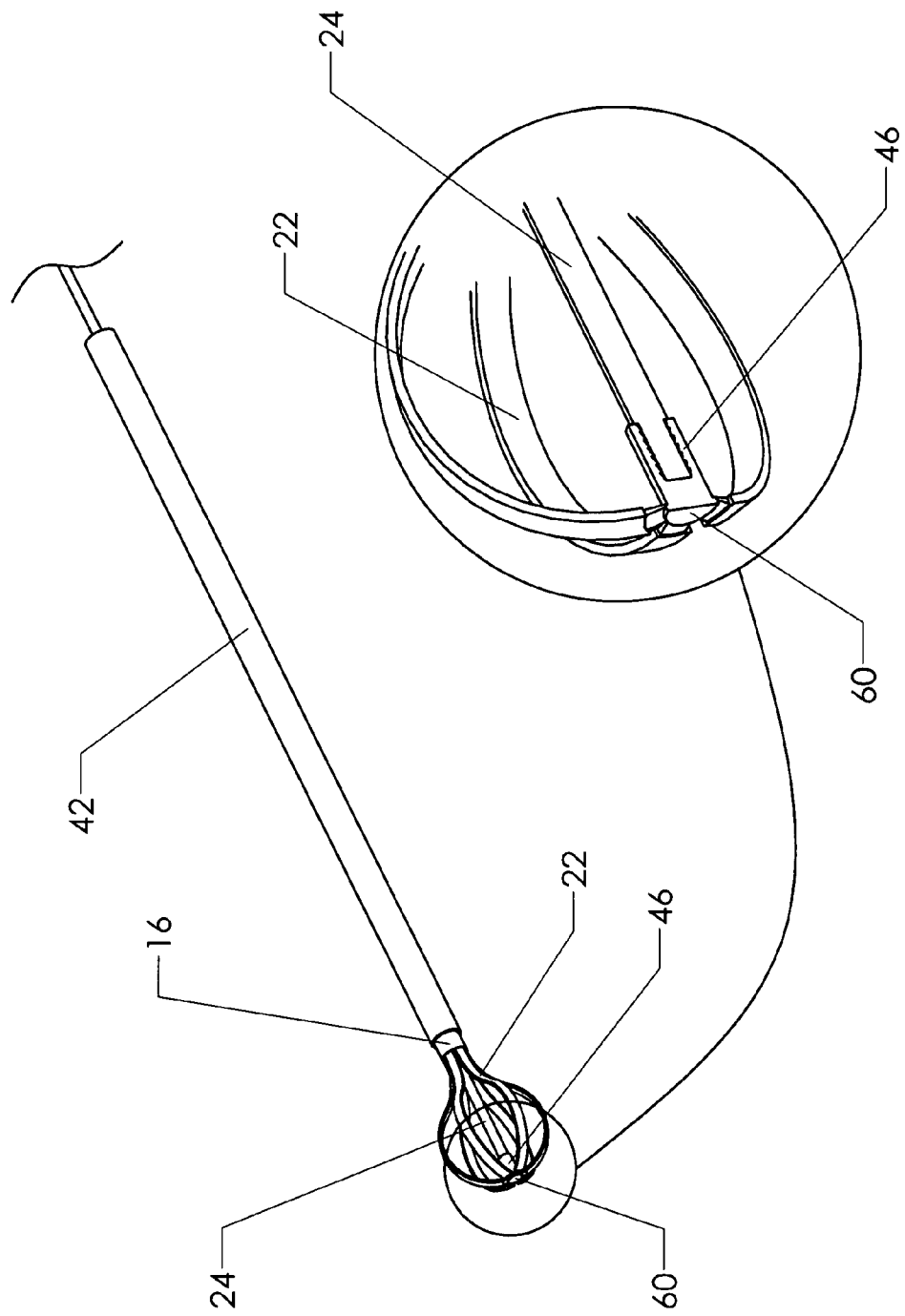
FIG. 5 is a perspective view, showing the spider assembly and how it relates to the inner tube.

FIG. 5 shows the assembly which is used to expand and contract spider 22. As discussed previously, the radial springs of spider 22 are each connected at their distal ends to hub 60 and at their proximal ends to locking collar 16. Locking collar 16 is attached to inner tube 42, which is a long hollow tube. Locking collar 16 may in fact simply be an integral part of inner tube 42. Mechanical assist rod 24 passes through inner tube 42 and connects to hub 60. The detail view shows how fastener 46 is used to connect the mechanical assist rod to the spider. Many types of fasteners could be used.

Those skilled in the art will readily appreciate the operational implications of the assembly shown in FIG. 5. If the mechanical assist rod is pulled through the inner tube to the right in the orientation shown in the view, hub 60 will be forced toward locking collar 16. This motion will cause spider 22 to progressively expand into the balloon shape shown.

Figure 6:
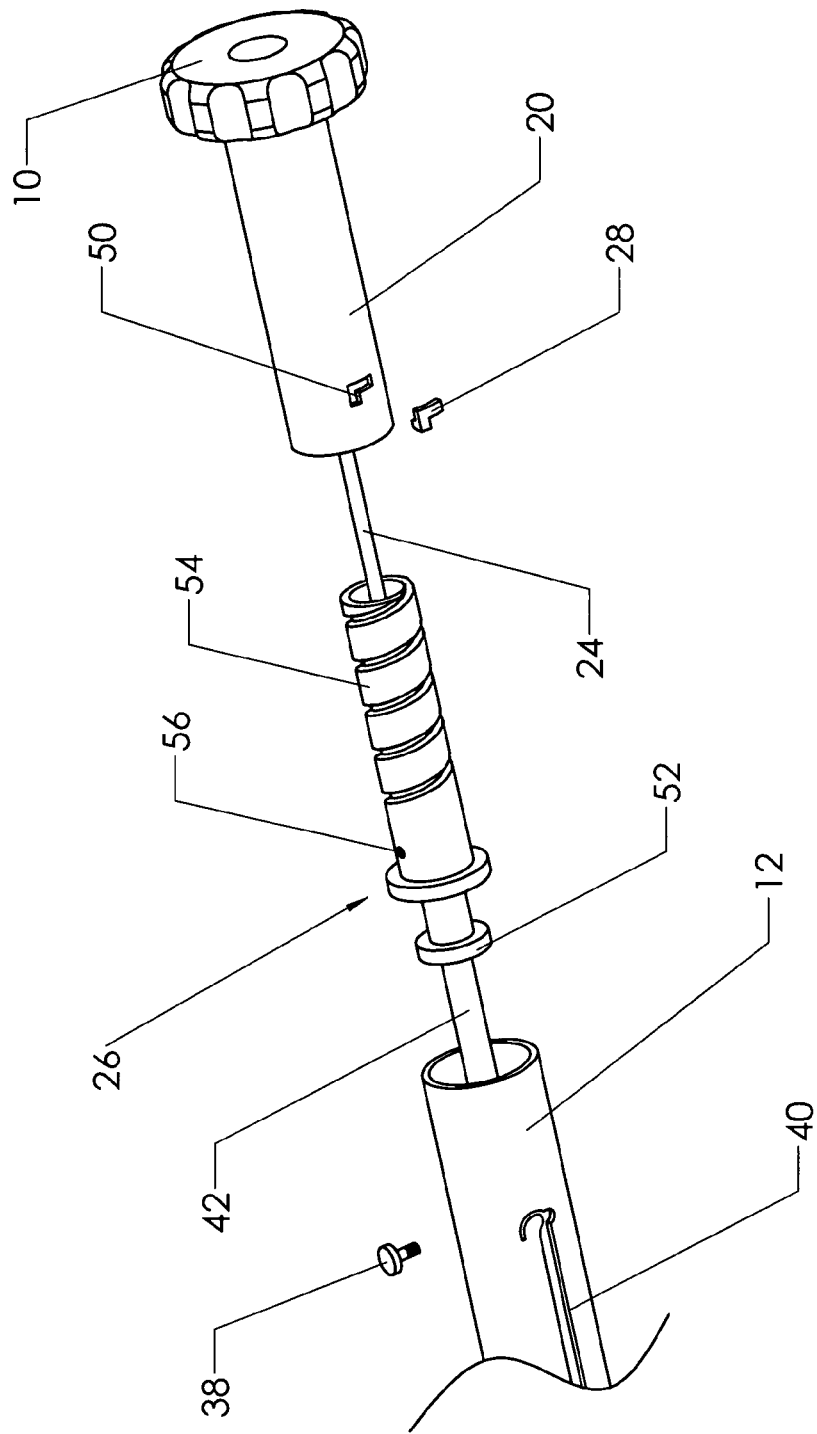
FIG. 6 is an exploded perspective view, showing the components located on the invention's proximal end.

FIG. 6 is an exploded view showing the features used to deploy and expand the spider, all of which are located on the invention's proximal end. Handle 12 provides a gripping surface for a surgeon to hold and manipulate the invention. It is essentially a hollow tube, with a lever slot 40 opening through its side wall. Inner tube 42 passes through its hollow interior toward the distal end of the device. Actuator 26 is joined to inner tube 42. The actuator and inner tube may in fact be formed as a single integral piece.

Mechanical assist rod 24 passes out the open proximal end of actuator 26. Adjuster 20, which is still another hollow cylindrical component, is configured to slip over the exterior of the threaded portion of actuator 26. The adjustor's side wall opens into adjuster slot 50, which is configured to receive thread engaging key 28. The thread engaging key includes an inward-facing extension configured to engage helical thread 54 in actuator 26. The proximal end of adjuster 20 includes expansion knob 10, which preferably has gripping features.

Figure 7:
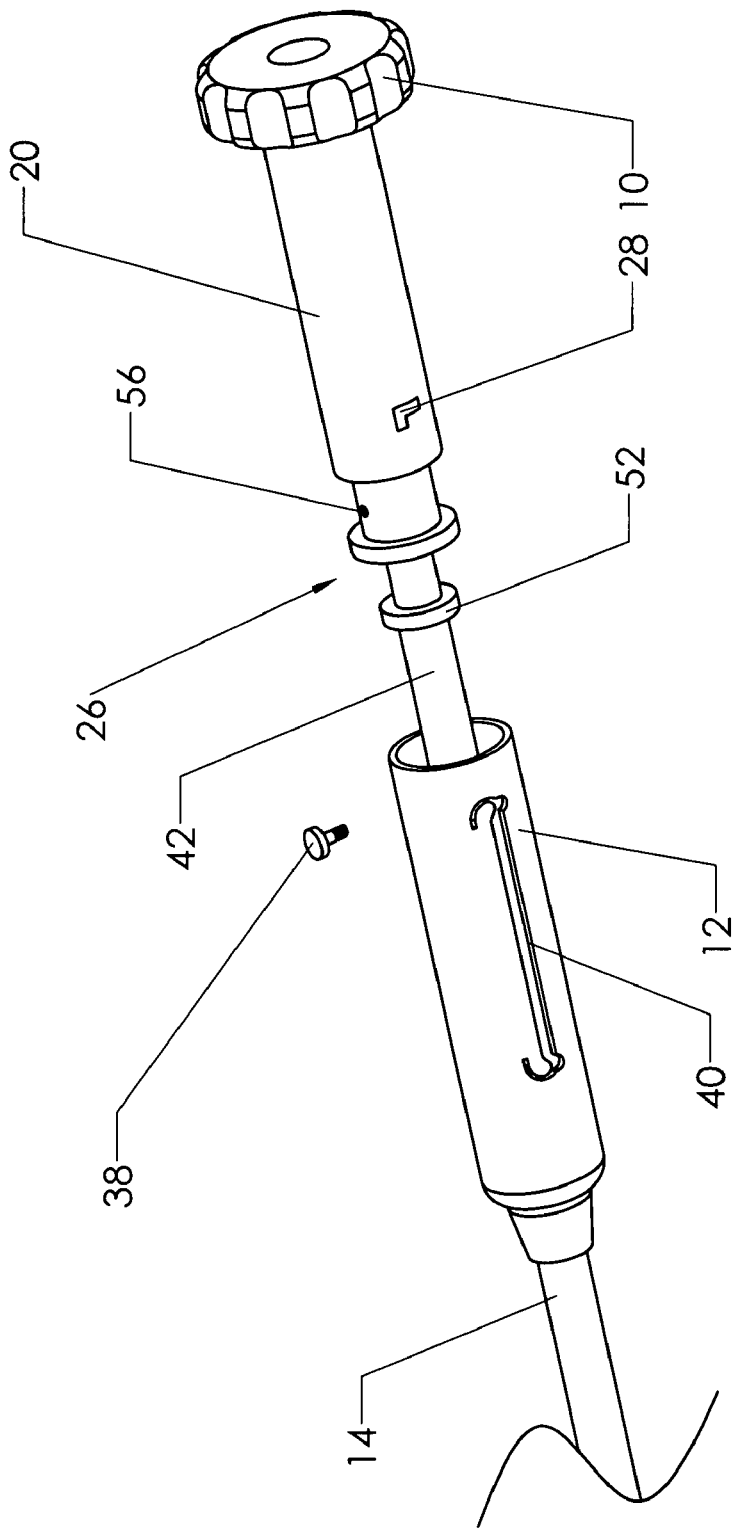
FIG. 7 is an exploded perspective view, showing the components located on the invention's proximal end.
Figure 8:
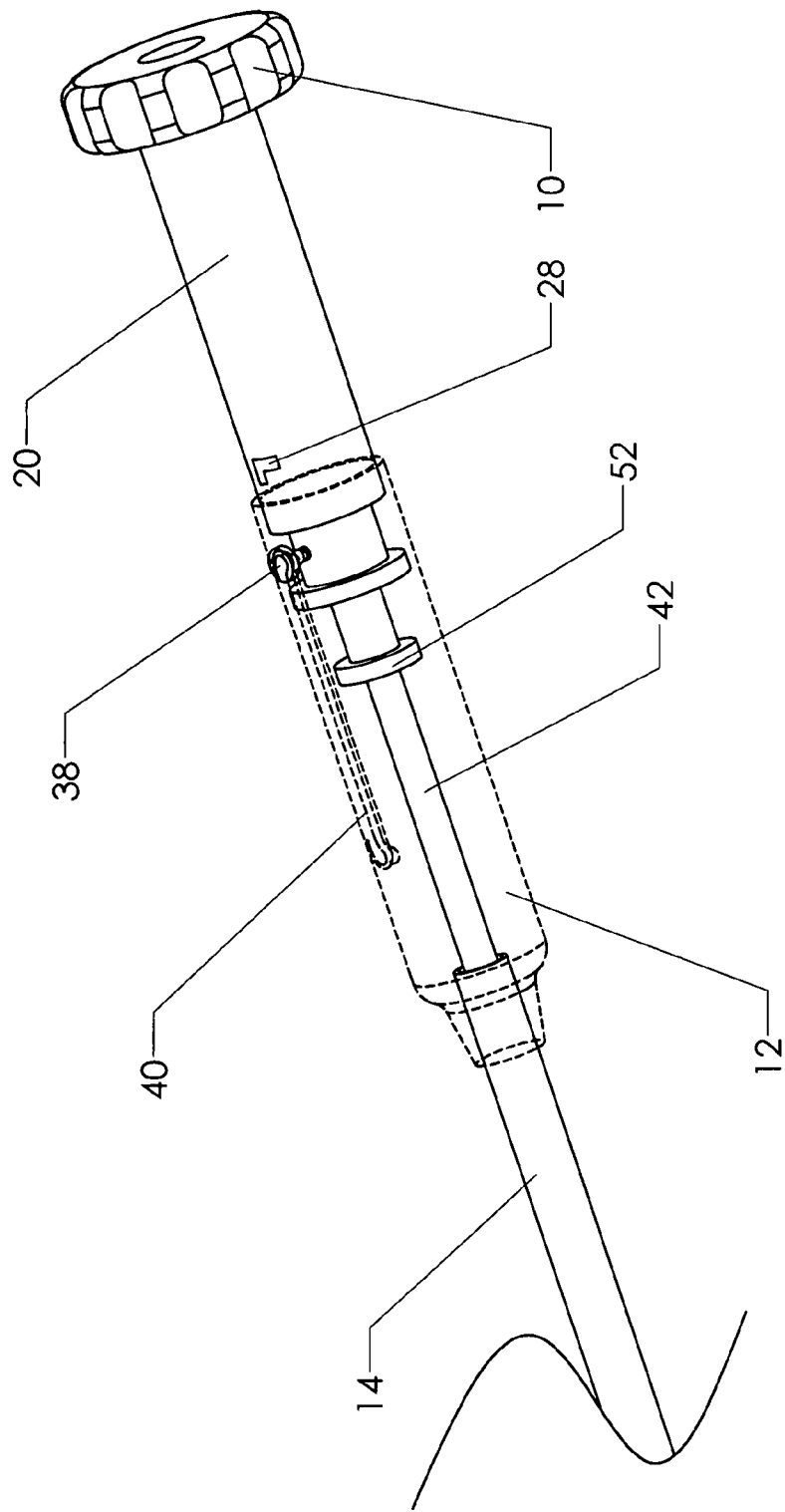
FIG. 8 is a perspective view, showing the components located on the invention's proximal end.

FIG. 7 shows the same assembly after adjuster 20 has been slipped over actuator 26 and thread engaging key 28 has been pressed into place. FIG. 8 shows the same assembly after adjuster 20 and actuator 26 have been pushed down into the hollow interior of handle 12 (Handle 12 is shown as hidden lines). At this point, lever 38 may be inserted through lever slot 40 and into lever receiver 56 in actuator 26. Those skilled in the art will realize that this action effectively locks the handle, the actuator, and the adjuster together.

The interaction between lever 38 and lever slot 40 allows the adjuster assembly to move between two states with respect to the handle. FIG. 8 shows the first of these two states. The reader will observe how the lever slot includes two notches—one at the proximal end of the handle and one closer to the distal end of the handle. The lever can be rotated into one of these notches to lock the adjuster assembly in one of two positions. In FIG. 8, lever 38 has been placed in the proximal notch. This leaves the adjuster and expansion knob protruding significantly from the proximal end of the handle.

Figure 9:
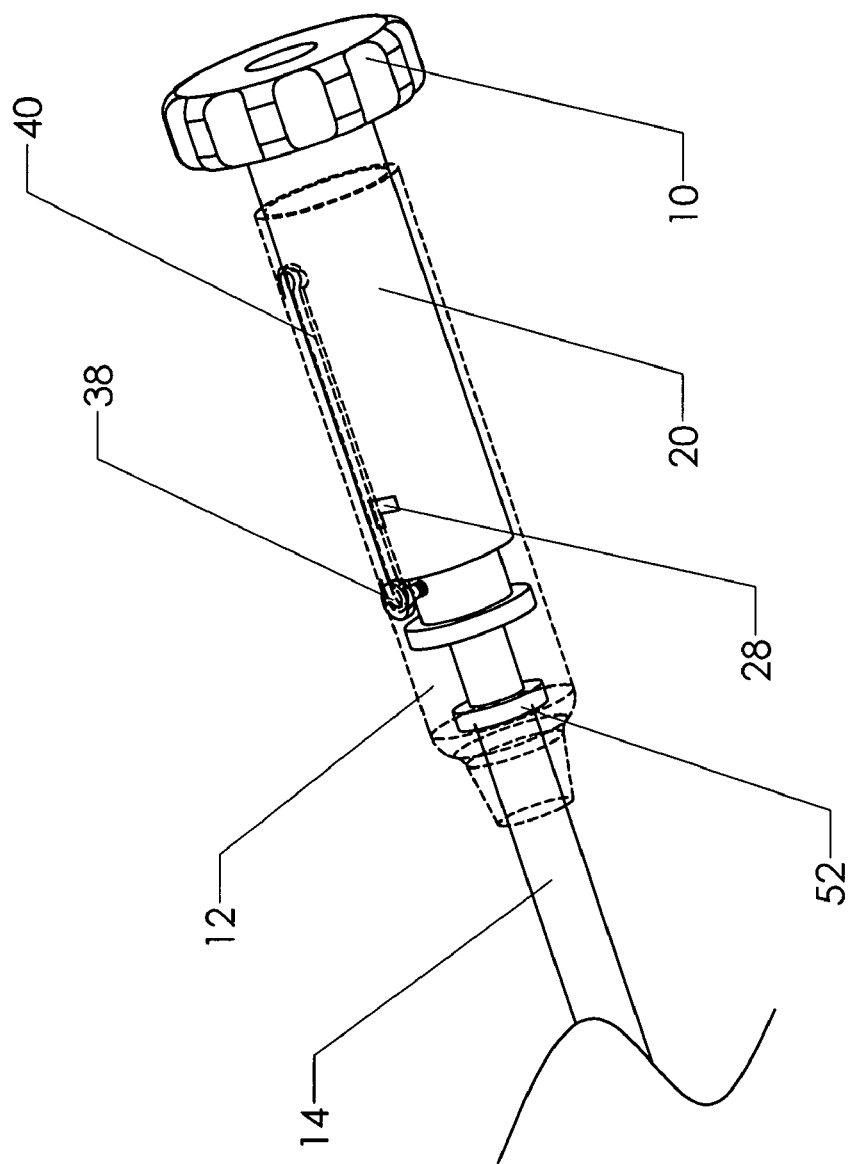
FIG. 9 is a perspective view, showing the components located on the invention's proximal end.

In FIG. 9, the user has grasped lever 38 and manipulated it so that it has moved into the long portion of lever slot 40 and then toward the distal end of the lever slot. After reaching the lever slot's distal end, lever 38 has been placed in the distal notch. This action locks the adjuster assembly in a second state, in which the adjuster and the expansion knob have moved toward the distal end of the handle. The reader will thereby appreciate how the interaction of the lever and the lever slot allows the device to be "indexed" between two different states. Those skilled in the art will realize that many other devices could be employed to create this indexing feature, with a spring plunger engaging a pair of detents being a good alternative example.

Figure 11:
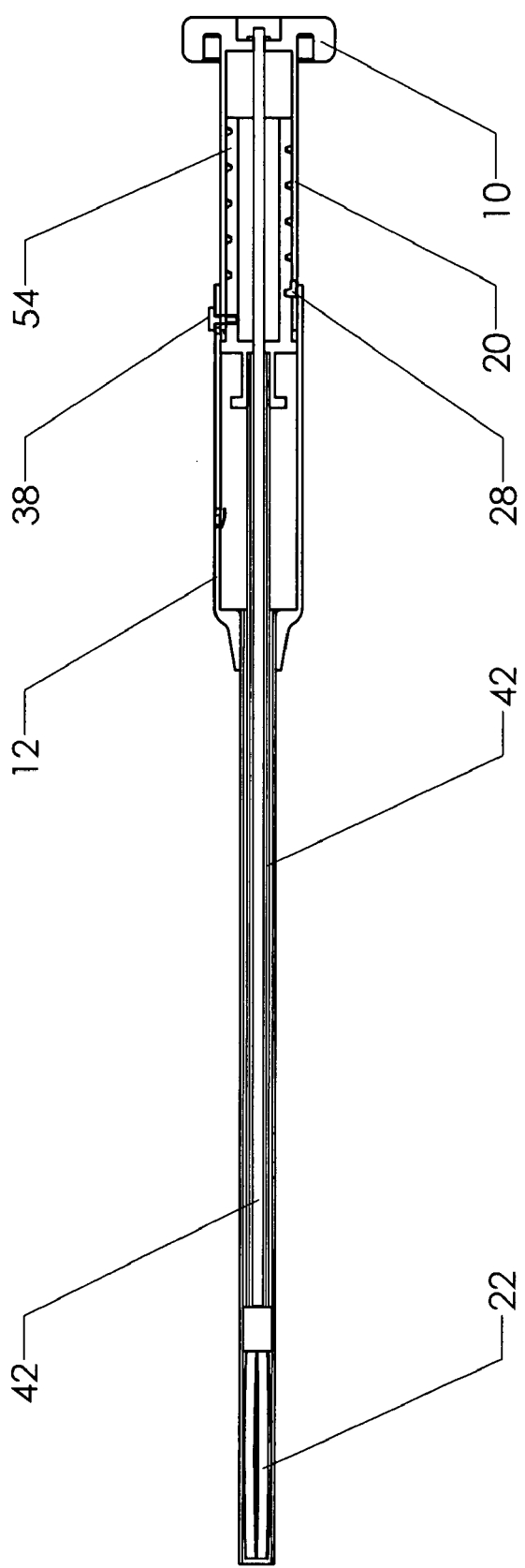
FIG. 11 is a section view, showing the entire invention with the spider collapsed and retracted in the cannula.
Figure 12:
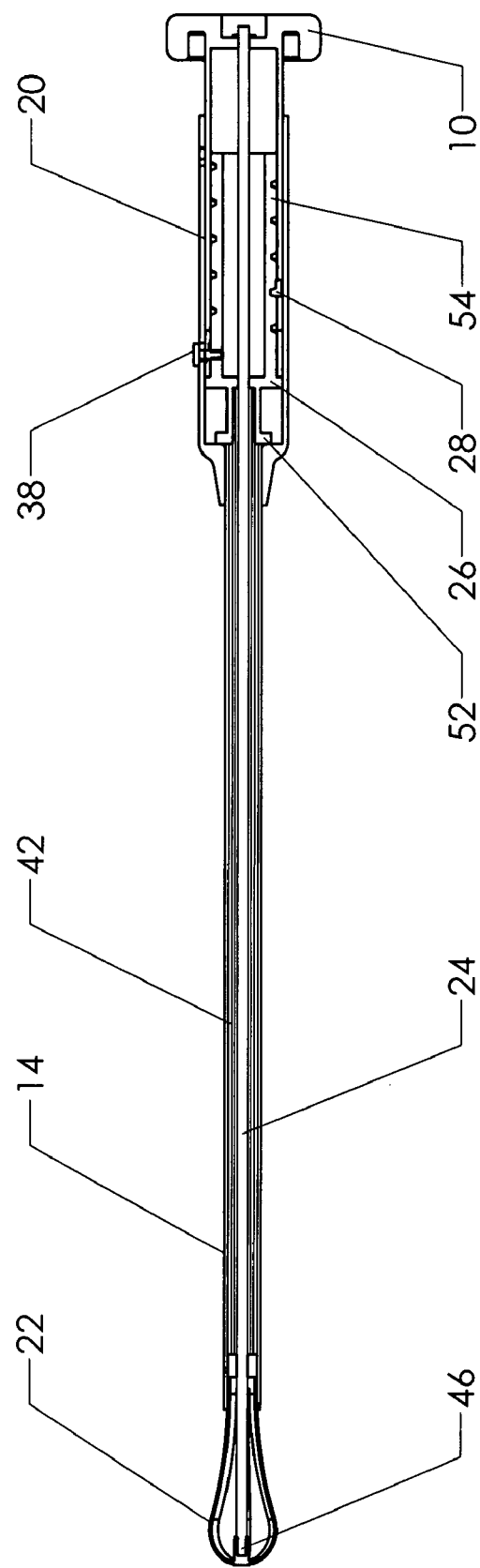
FIG. 12 is a section view, showing the spider extended and partially expanded.

FIGS. 11 and 12 serve to illustrate the significance of the two indexed positions. FIG. 11 is a section view through the entire invention, in which the adjuster assembly is indexed to the position where adjuster 20 and expansion knob 10 protrude well clear of the proximal end of handle 12. Lever 38 rests within the proximal notch of the lever slot.

Cannula 14 extends away from the distal end of handle 12 toward the distal end of the device. It contains inner tube 42 and mechanical assist rod 24. In the indexed position shown, spider 22 is also contained within the cannula in a collapsed state. If the user manipulates the lever to place the lever within the distal notch of the lever slot, spider 22 will be pushed clear of the cannula. FIG. 12 shows the invention after the lever has been manipulated to lie in the distal notch of the lever slot. The reader will observe how the spider has been pushed clear of the cannula. The surgeon may then manipulate expansion knob 10 to expand the spider (it is shown partially expanded in the view).

Figure 10:
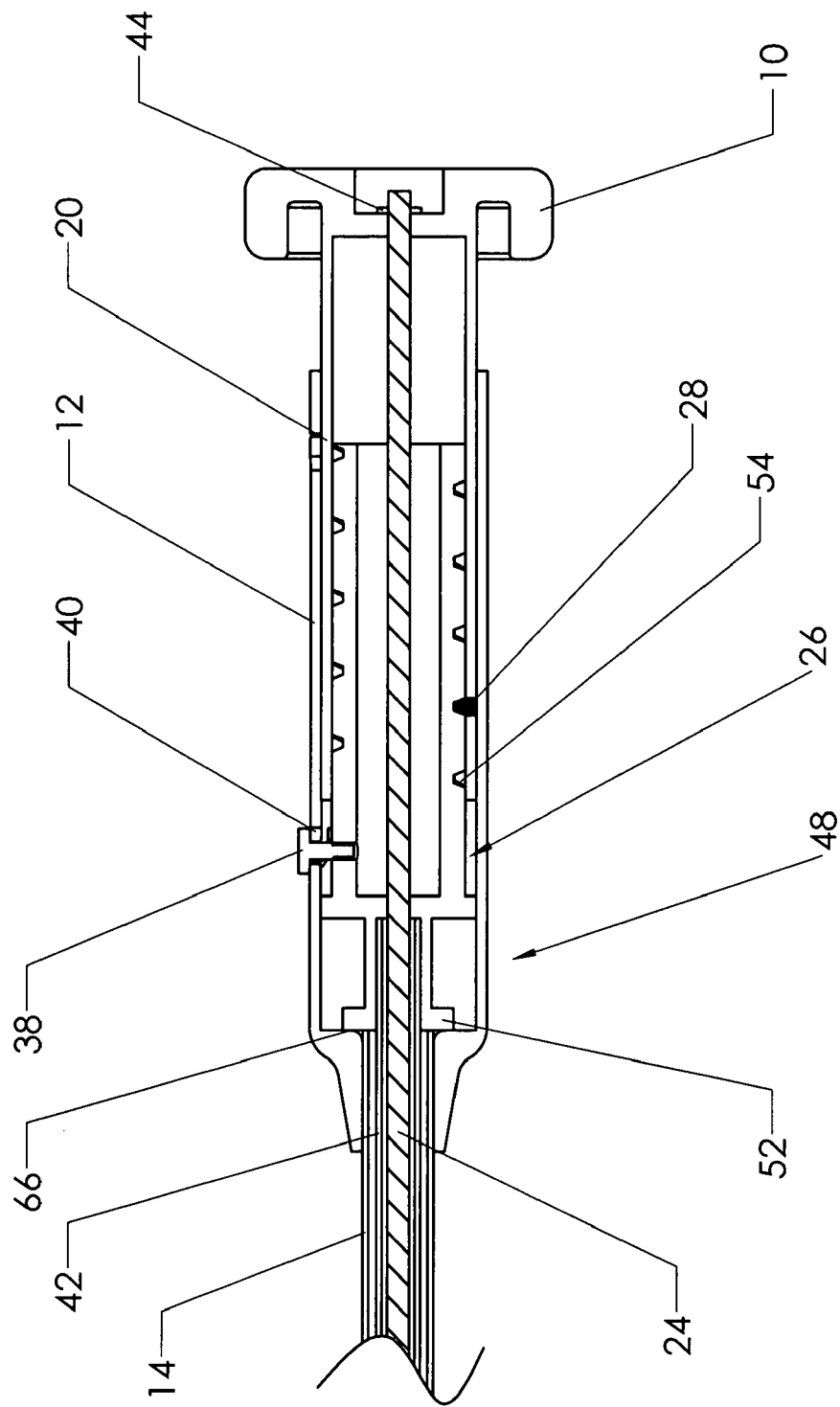
FIG. 10 is a section view, showing the components located on the invention's proximal end.

Turning now to FIG. 10, the spider's deployment will be explained in more detail. FIG. 10 is a section view showing the handle, the adjuster, and associated components. Lever 38 is shown positioned in the distal notch of the lever slot. In this position, actuator 26 has moved toward the distal end of the device. Thrust flange 52 bears against end wall 66 of handle 12, thereby preventing further distal motion of the actuator with respect to the handle. It is thereby "anchored" against the handle.

If the user then rotates adjuster 20 by gripping expansion knob 10, thread engaging key 28 will engage helical thread 54 in actuator 26 and cause adjuster 20 to move proximally and distally with respect to the actuator and the handle (depending on whether the thread is a right-hand or left-hand thread and depending upon the direction of rotation of the expansion knob). Mechanical assist rod 24 is linked to the expansion knob, preferably by a rotating joint such as washer 44. Moving the adjuster in and out of the device thereby causes mechanical assist rod 24 to move in and out of the device. The distal end of the mechanical assist rod is attached to the spider. The motion thus described will therefore expand and contract the spider.

In one alternative embodiment the adjuster could contain hash-marks on its body which measure the relative expansion of the abrasive tip. As the adjuster moves in and out of the handle, the user would observe the hash-marks in relation to the handle describing the degree to which the balloon had expanded. A window on the handle could be installed to view the hash-marks through, as the adjuster turns, in order to more easily read the measurement.

Figure 13:
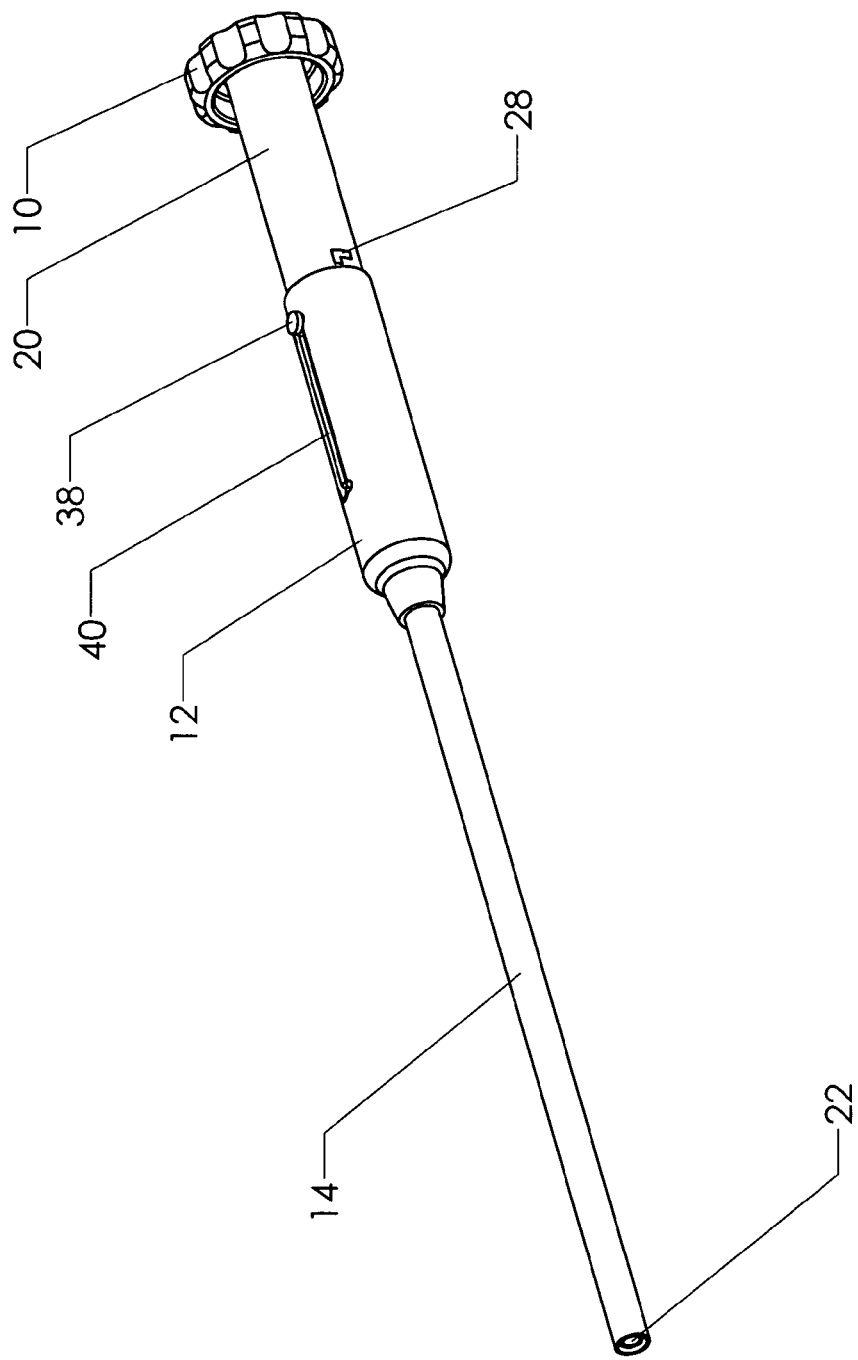
FIG. 13 is a perspective view, showing the entire invention with the spider collapsed and retracted.
Figure 14:
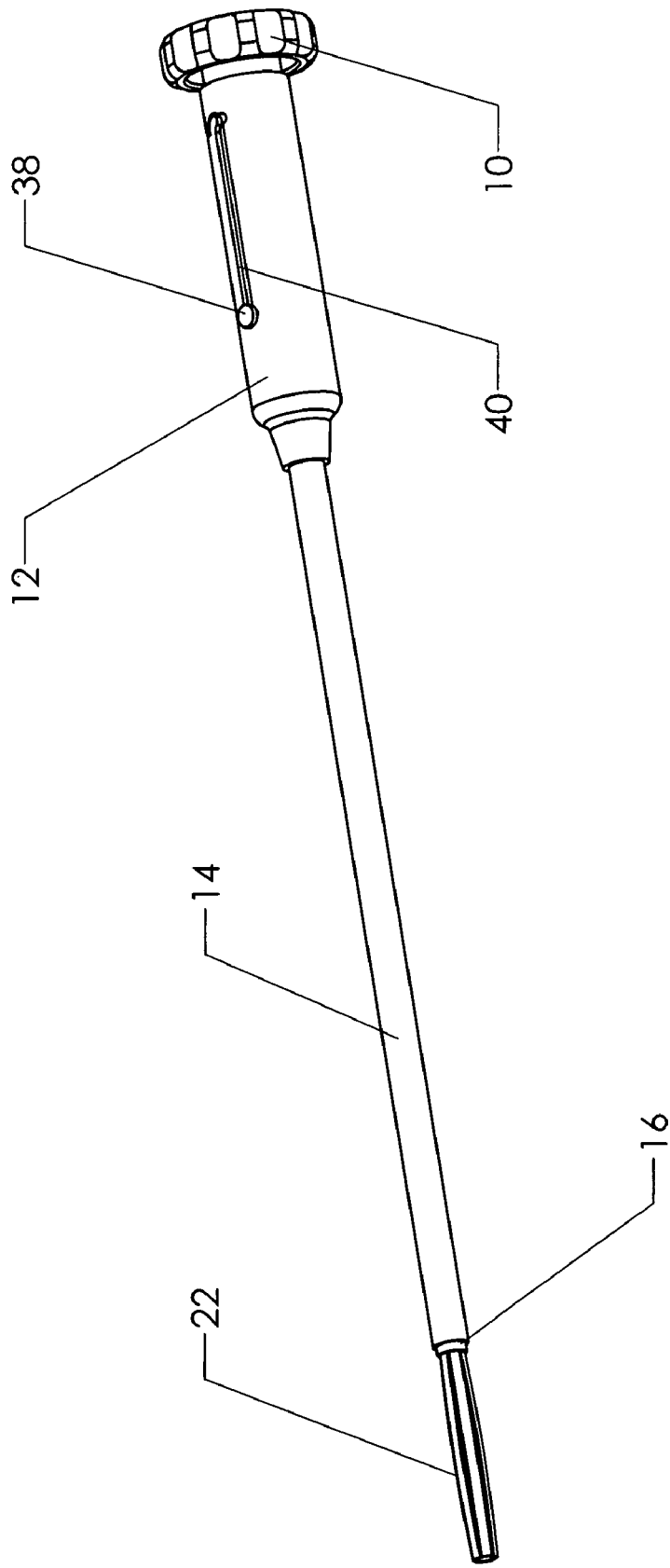
FIG. 14 is an elevation view, showing the spider extended but not expanded.

FIG. 13 shows a perspective view of the device with the spider retracted into the cannula. In this state the surgeon can insert the cannula through a thoracoport in the patient's chest. The surgeon would then use the lever to "index" the device to the deployed state in which the collapsed spider extends beyond the end of the cannula. The deployed state is shown in FIG. 14. The reader will observe that the lever is locked into the distal notch of the lever slot.

Figure 15:
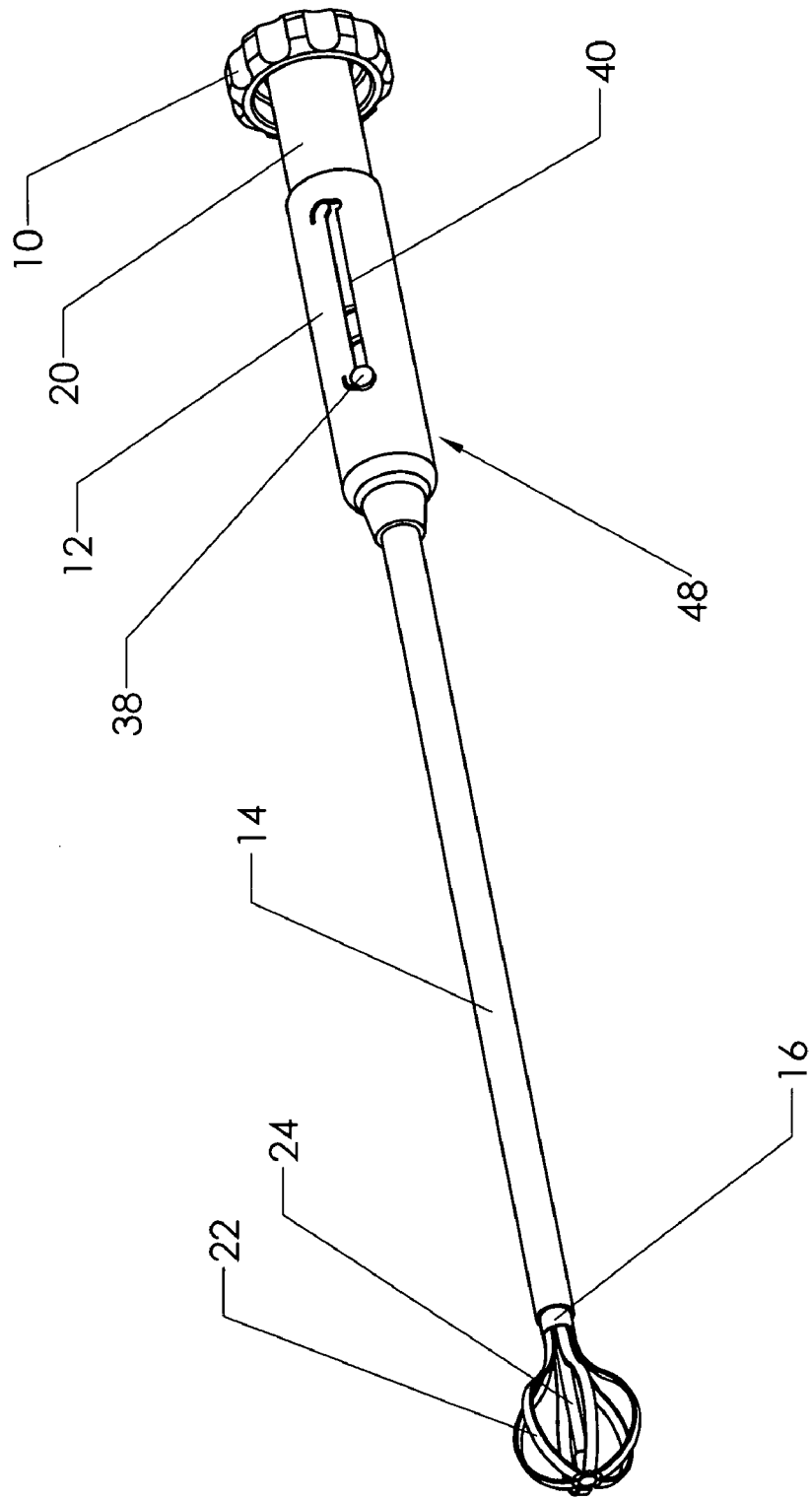
FIG. 15 is a perspective view, showing the spider extended and expanded.
Figure 16:
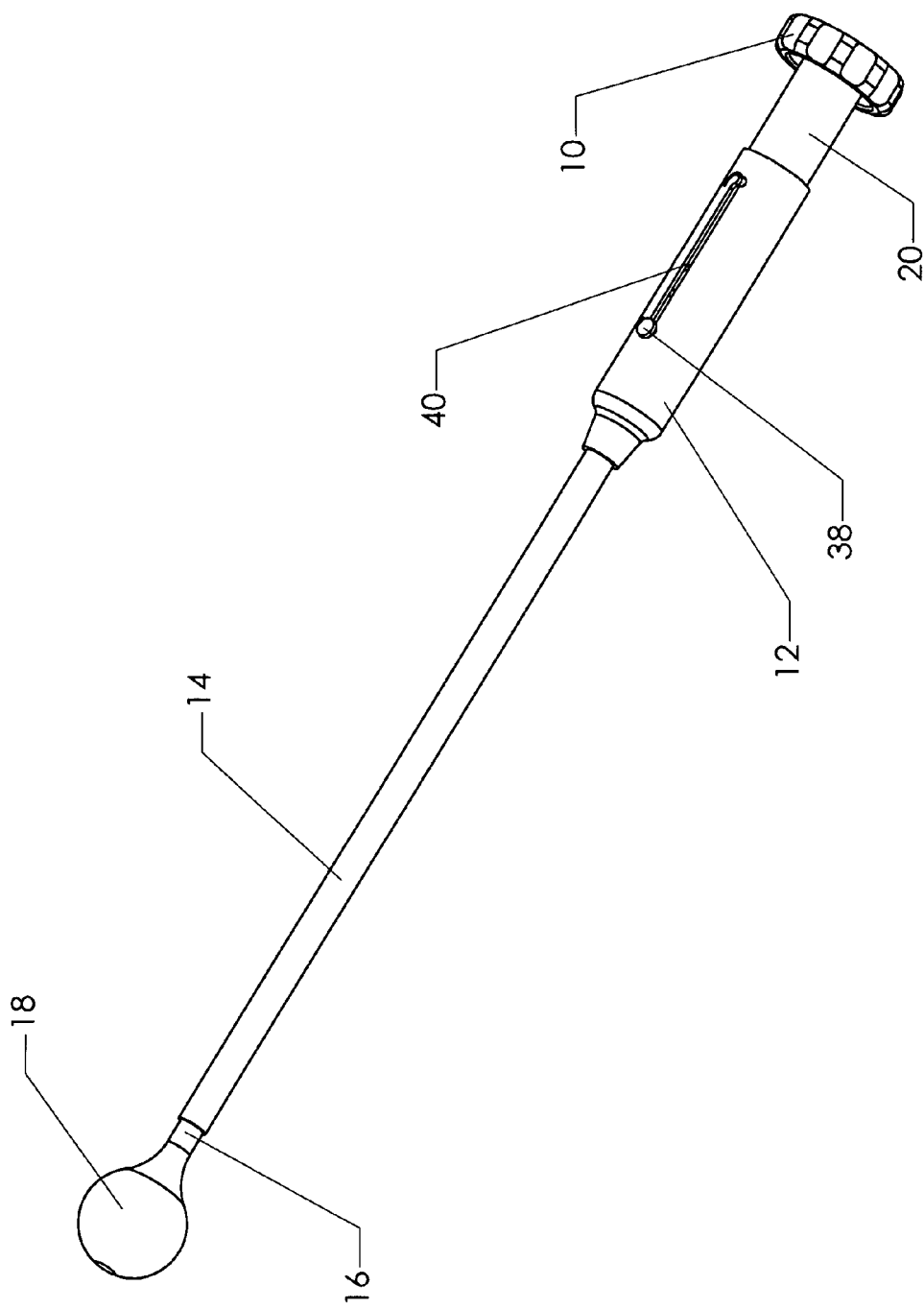
FIG. 16 is a perspective view, showing the spider extended and expanded.

The spider is fully deployed, but is still in a collapsed state. The surgeon then rotates expansion knob 10 in the appropriate direction to expand and contract the spider as desired. FIG. 15 shows spider 22 in a fully expanded state suitable for use. Of course—as mentioned previously—the radial springs of the spider are preferably covered with an abrasive material in use. FIG. 16 shows how abrasive tip 18 covers the radial springs and provides a smoother external contour. The abrasive tip is preferably an elastic material which will fit tightly over the spider's frame in both a collapsed and expanded state. It is preferably coated with an appropriate surface texture to facilitate the abrading operation. The material is preferably absorptive as well as abrasive.

Once the surgeon completes the abrading operation, the expansion knob is rotated in the appropriate direction to collapse the spider. The lever is then indexed toward the proximal position in order to withdraw the spider into the distal end of the cannula. The entire device may then be pulled back out through the thoracoport (or conventional incision if no thoracoport is used).

Many suitable materials can be used to make the components of the device. One should bear in mind, however, the need for complete disposal of the device. Thus, all of the components are preferably made of disposable materials which can be thrown away after every use. Alternatively, many components of the device could be made of stainless steel so as to allow for repeated sterilization of the device. In this embodiment, other components—such as the abrasive tip—are preferably made of disposable materials which will be replaced after every use.

The preceding description contains significant detail regarding the novel aspects of the present invention. It should not be construed, however, as limiting the scope of the invention but rather as providing illustrations of the preferred embodiments of the invention. As an example, the expansion and deflation of spider 22 could be accomplished by pushing and pulling expansion knob 10 and adjuster 20 utilizing a spring activated adjusting nut as opposed to a fixed adjusting nut. As an additional example, a cable could be substituted for the mechanical assist rod (provided that the radial springs were strong enough to maintain tension on the cable). Different mechanisms could also be used for the deflation or expansion of spider 22. Thus, the scope of the invention should be fixed by the following claims, rather than by the examples given.

We claim:

1. An expandable abrading device, comprising:
   a. a handle having a hollow interior, a proximal end, and a distal end;
   b. a cannula, having a hollow interior, a proximal end and a distal end, with a proximal opening proximate said proximal end and a distal opening proximate said distal end, said proximal end being joined to said handle with said proximal opening joining said hollow interior of said handle;
   c. an adjuster, having a hollow interior, said adjuster being slidably located within said hollow interior of said handle;
   d. an actuator, slidably located within said hollow interior of said adjuster, said actuator having a passage;
   e. an inner tube attached to said actuator and extending through said hollow interior of said cannula, said inner tube having a proximal end attached to said actuator and a distal end distal to said actuator;
   f. a spider assembly including,
      i. a locking collar attached to said distal end of said inner tube,
      ii. a hub, and
      iii. a plurality of radial springs connecting said locking collar to said hub;
   g. a rotation-limiting connection between said handle and said actuator, so that rotation between said handle and said actuator is limited;
   h. a threaded engagement between said adjuster and said actuator, configured so that rotating said adjuster with respect to said handle causes said adjuster to move linearly with respect to said actuator;
   i. a mechanical link between said actuator and said handle, said mechanical link configured to lock said actuator in a first state in which said actuator is moved away from said distal end of said handle and a second state in which said actuator is moved toward said distal end of said handle;

j. wherein said components are sized such that in said first state said spider assembly lies within said cannula and in said second state said spider assembly extends beyond said distal opening of said cannula; and k. a mechanical assist rod connecting said hub to said adjuster, said mechanical assist rod passing through said passage in said actuator, said mechanical assist rod being attached to said adjuster so that rotating said adjuster in a first direction with respect to said handle draws said hub toward said locking collar, thereby expanding said plurality of radial springs, and rotating said adjuster in a second direction with respect to said handle forces said hub away from said locking collar, thereby retracting said plurality of radial springs.

2. The expandable abrading device of claim 1, further comprising an abrasive tip covering said plurality of radial springs.

3. The expandable abrading device of claim 2, wherein said plurality of radial springs are configured to accept an elastic abrasive outer covering.

4. The expandable abrading device of claim 1, wherein said handle includes an end wall and said actuator includes a thrust flange configured to bear against said end wall.

5. The expandable abrading device of claim 4, wherein said mechanical link between said actuator and said handle comprises a lever attached to said actuator resting within a slot in said handle.

6. The expandable abrading device of claim 1, wherein said actuator further comprises
  a. a thrust flange; and
  b. wherein said thrust flange is configured to prevent said actuator from entering said proximal end of said cannula.

7. The expandable abrading device of claim 1, wherein said mechanical link between said actuator and said handle comprises a lever attached to said actuator resting within a slot in said handle.

8. The expandable abrading device of claim 1, further comprising an expansion knob located on said proximal end of said adjuster, said expansion knob having an enlarged diameter.

9. The expandable abrading device of claim 1, wherein said handle further comprises a lever slot, having a proximal notch and a distal notch.

10. The expandable abrading device of claim 9, further comprising a lever attached to said actuator, said lever configured to enter and lock in place at said proximal notch and said distal notch of said lever slot.

11. The expandable abrading device of claim 8, wherein said expansion knob includes a plurality of gripping features.

12. The expandable abrading device of claim 4, further comprising an abrasive tip covering said plurality of radial springs.

13. The expandable abrading device of claim 5, further comprising an abrasive tip covering said plurality of radial springs.

14. The expandable abrading device of claim 1, wherein said threaded engagement between said actuator and said adjuster comprises:
  a. a threaded portion on said actuator;
  b. a thread engaging key configured to attach to said adjuster and engage said threaded portion of said actuator; and
  c. wherein when said adjuster rotates about said actuator said thread engaging key moves around said threaded portion of said actuator thereby translating said adjuster towards or away from said proximal end of said cannula.

15. The expandable abrading device of claim 2, wherein said abrasive tip is an elastic material configured to fit tightly over said plurality of radial springs.

16. An expandable abrading device, comprising:
  a. a handle having a hollow interior, a proximal end, and a distal end;
  b. a cannula, having a hollow interior, a proximal end and a distal end, with a proximal opening proximate said proximal end and a distal opening proximate said distal end, said proximal end being joined to said handle with said proximal opening joining said hollow interior of said handle;
  c. an adjuster, having a hollow interior, said adjuster being slidably located within said hollow interior of said handle;
  d. an actuator, slidably located within said hollow interior of said adjuster, said actuator having a passage;
  e. an inner tube attached to said actuator and extending through said hollow interior of said cannula, said inner tube having a proximal end attached to said actuator and a distal end distal to said actuator;
  f. a spider assembly including,
    i. a locking collar attached to said distal end of said inner tube,
    ii. a hub, and
    iii. a plurality of radial springs connecting said locking collar to said hub;
  g. an adjustable mechanical engagement between said adjuster and said actuator, configured to move said adjuster linearly with respect to said actuator;
  h. a mechanical link between said actuator and said handle, said mechanical link configured to lock said actuator in a first state in which said actuator is moved away from said distal end of said handle and a second state in which said actuator is moved toward said distal end of said handle;
  i. wherein said components are sized such that in said first state said spider assembly lies within said cannula and in said second state said spider assembly extends beyond said distal opening of said cannula; and
  j. a mechanical assist rod connecting said hub to said adjuster, said mechanical assist rod passing through said passage in said actuator, said mechanical assist rod being attached to said adjuster so that moving said adjuster away from said distal end of said handle draws said hub toward said locking collar, thereby expanding said plurality of radial springs, and moving said adjuster toward said distal end of said handle forces said hub away from said locking collar, thereby retracting said plurality of radial springs.

17. An expandable abrading device as recited in claim 16, further comprising an abrasive tip covering said plurality of radial springs.

* * * * *